United States Patent [19]

Harries

[11] 4,025,792

[45] May 24, 1977

[54] FILTERS FOR GAS DETECTORS

[75] Inventor: John Edward Harries, Teddington, England

[73] Assignee: The Secretary of State for Industry in Her Britannic Majesty's Government of the United Kingdom of Great Britain and Northern Ireland, London, England

[22] Filed: Sept. 2, 1975

[21] Appl. No.: 609,628

[30] Foreign Application Priority Data

Sept. 3, 1974 United Kingdom ............ 38485/74

[52] U.S. Cl. .............................. 250/343; 356/106 S
[51] Int. Cl.² ........................................ G01N 21/26
[58] Field of Search .......... 250/343, 344, 345, 346, 250/373, 340, 341; 356/106 S, 107

[56] References Cited

UNITED STATES PATENTS 3,381,134 4/1968 Wolf .................................. 356/107
3,723,731 3/1973 Blau ................................... 250/343

Primary Examiner—Craig E. Church
Attorney, Agent, or Firm—Cameron, Kerkam, Sutton, Stowell & Stowell

[57] ABSTRACT

A radiation filter, for a gas detector, comprising an optical interferometer having in each of first and second physically separated optical paths therethrough a gas cell containing a quantity of the gas to be detected; there being a difference in pressure between the quantities of gas in the two gas cells; the gas cells being of substantially equal lengths in the direction of the optical path therethrough; and the interferometer being arranged so that in the absence of the gas cells there is zero path difference between the said first and second optical paths through the interferometer.

12 Claims, 12 Drawing Figures

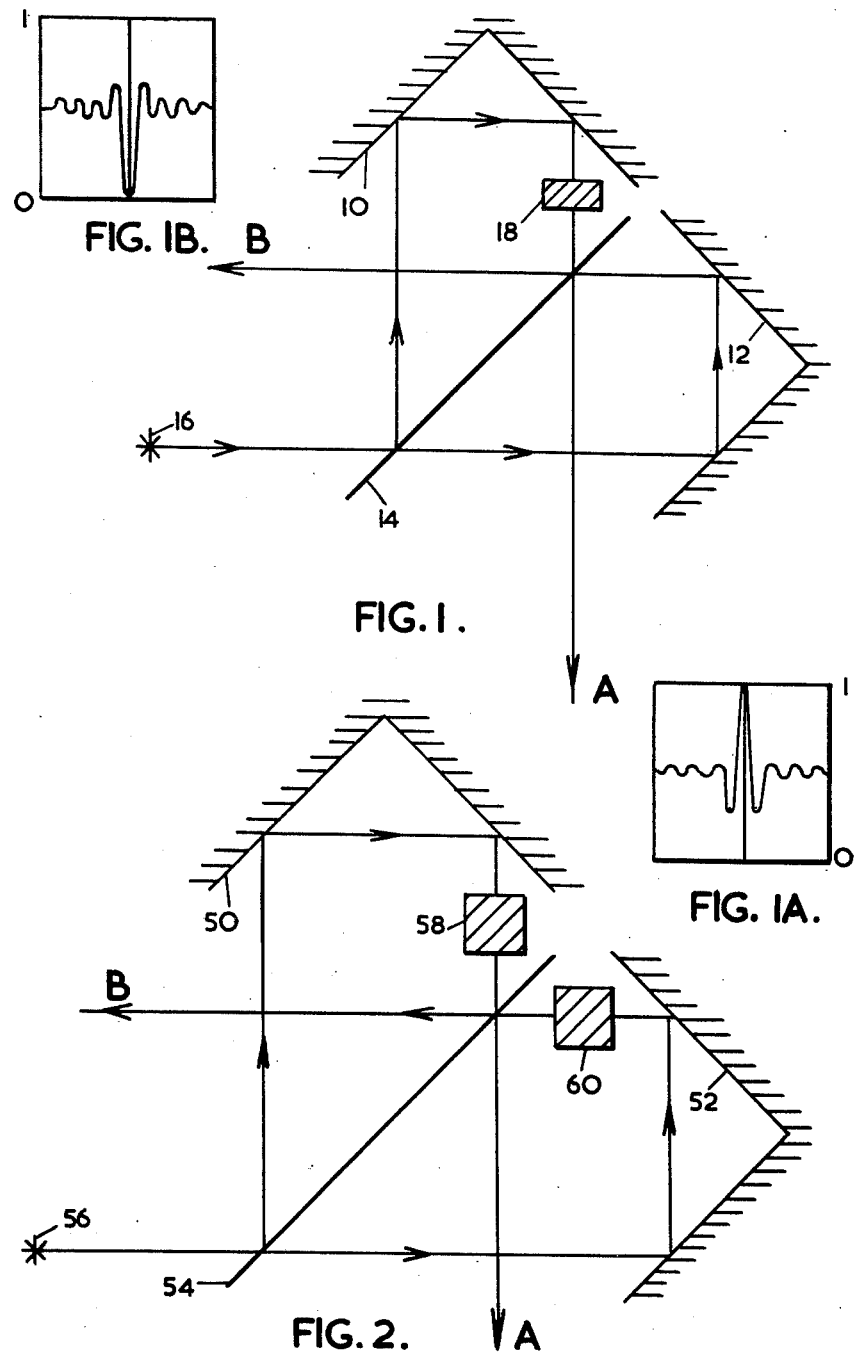

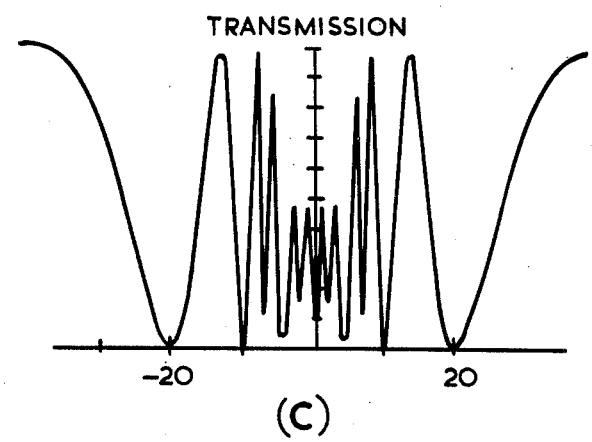
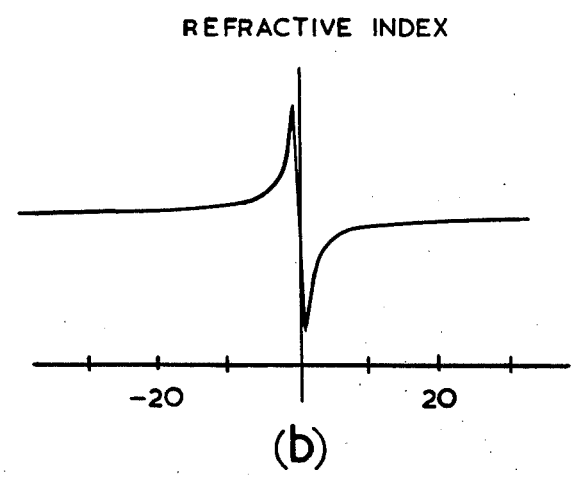
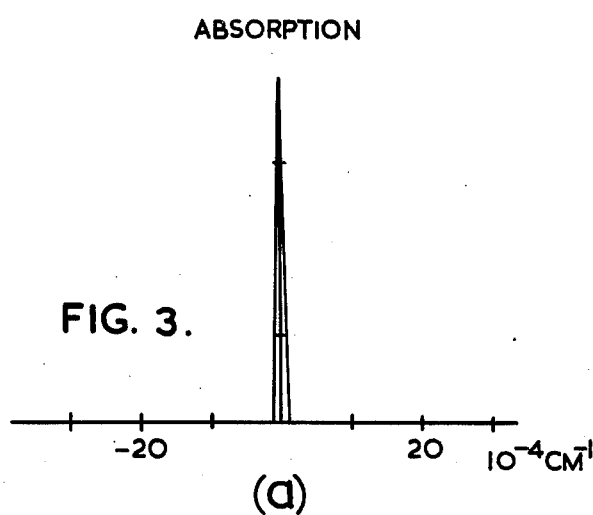
FIG. 3.

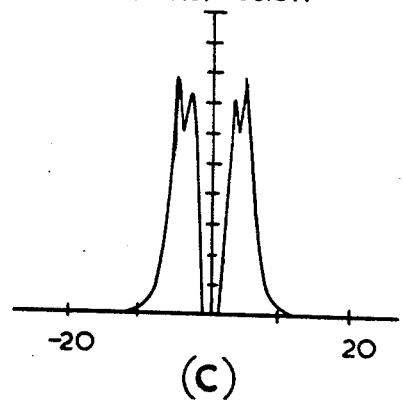
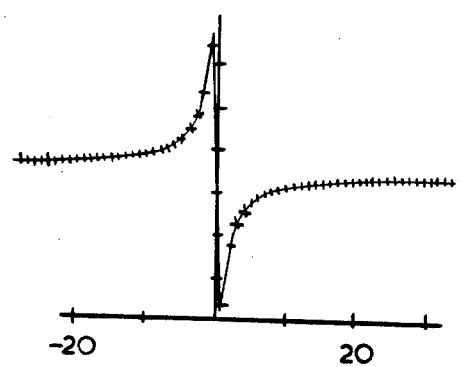
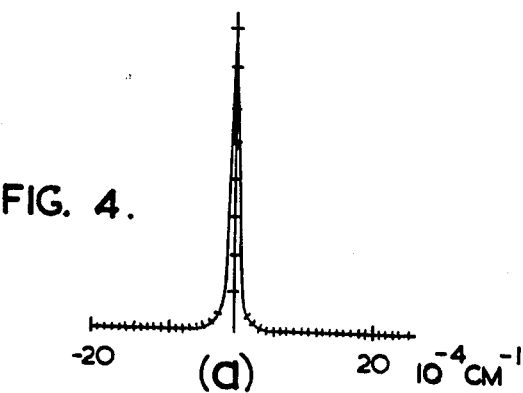
FIG. 4.

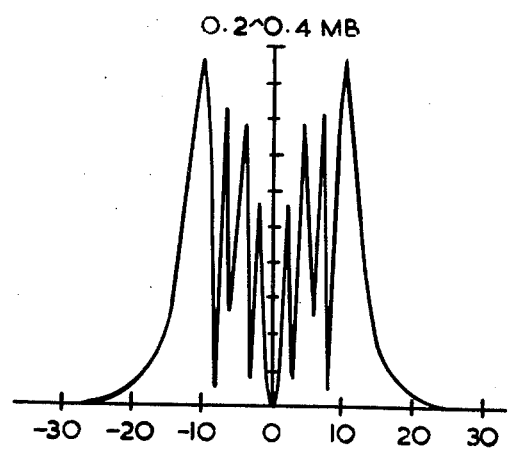
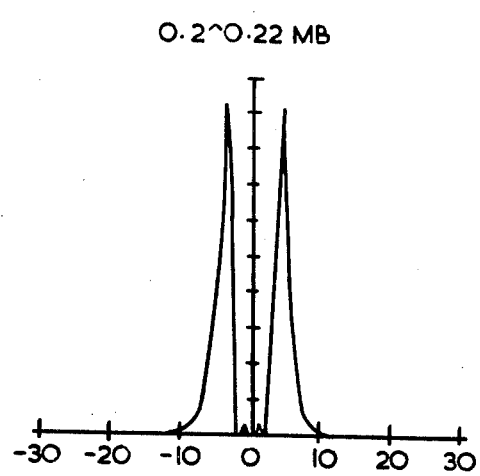
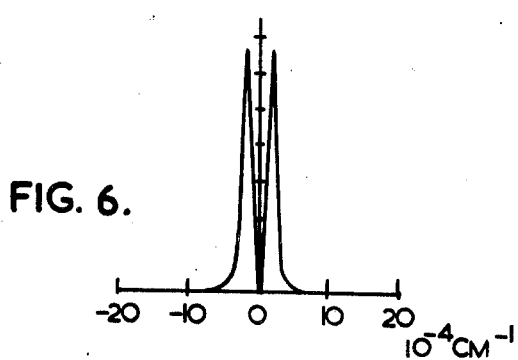
FIG. 6.

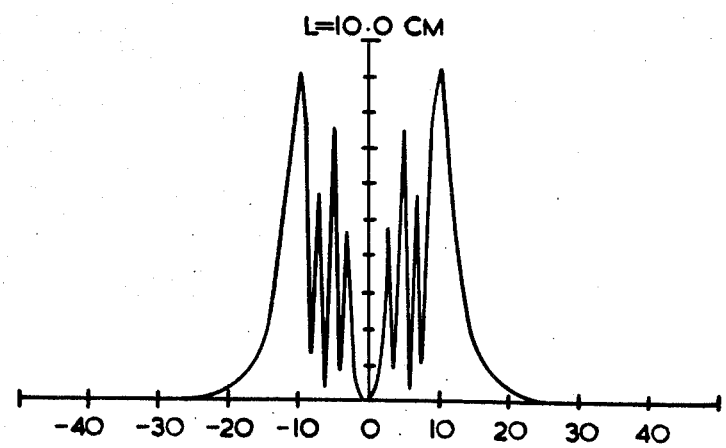
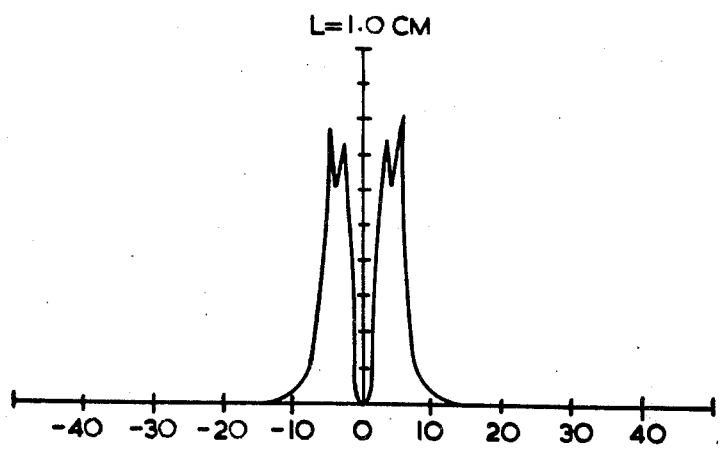
FIG. 7.
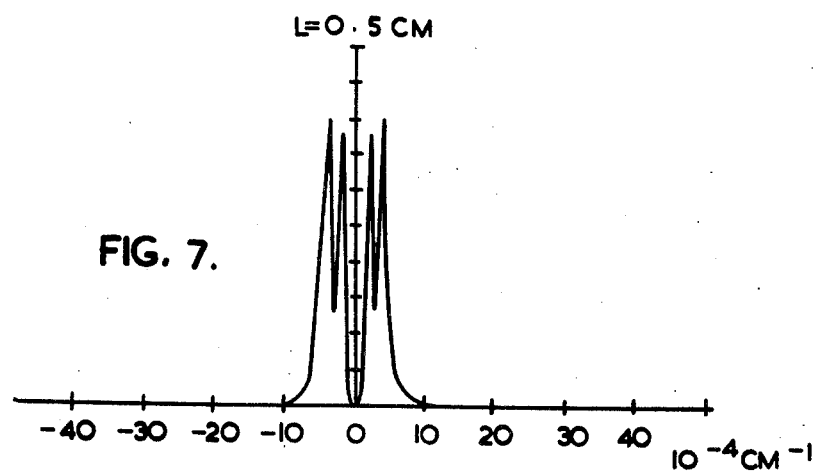

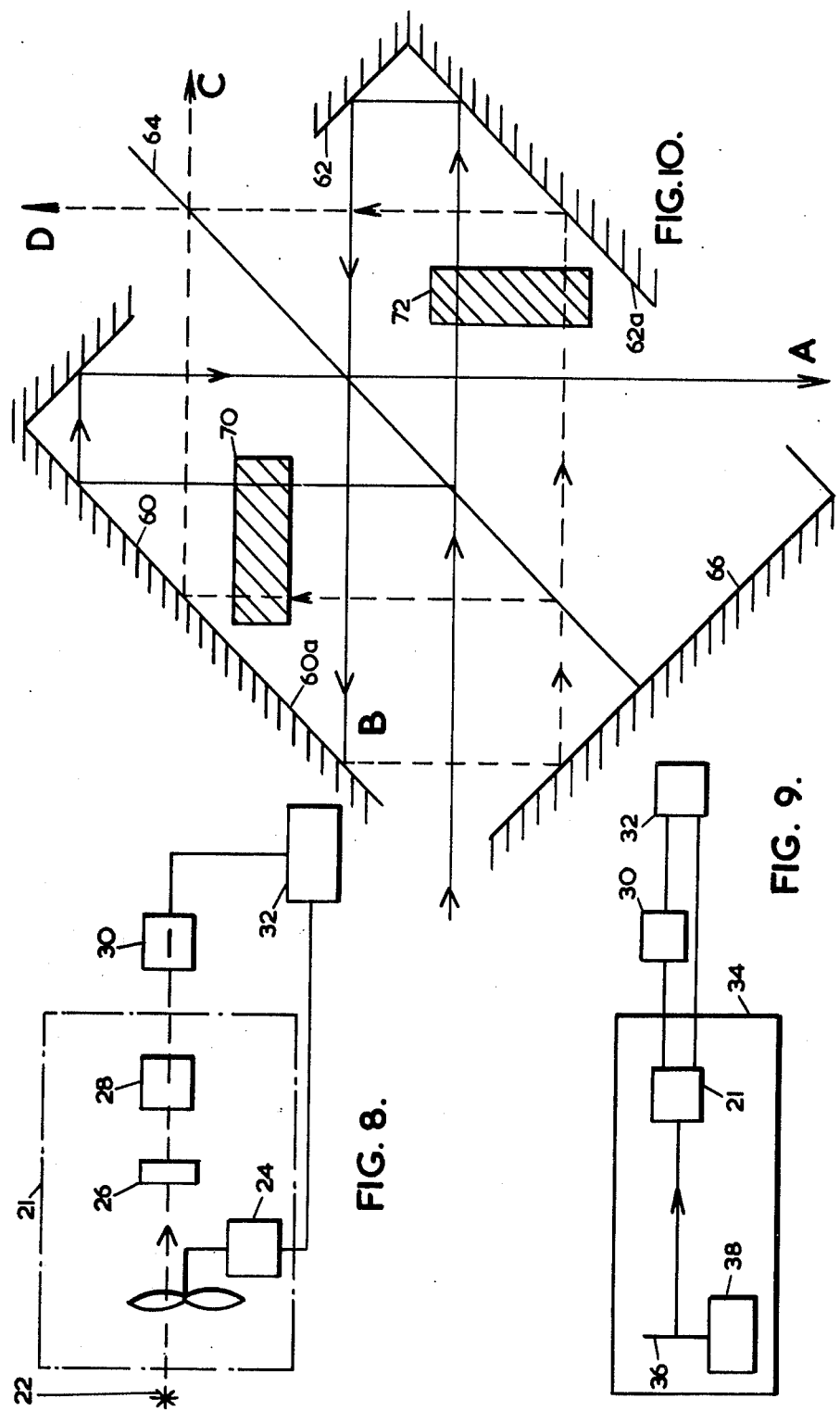

FILTERS FOR GAS DETECTORS

This invention relates to filters for gas detectors, more especially for absorption-line filter radiometers, which often operate an infra-red wavelengths.

When a gas in an atmosphere is to be detected or its concentration measured by an infra-red radiometer or spectrometer, it is essential to isolate radiation thermally emitted by the gas and this is often achieved by passing the radiation through a suitable infra-red filter before it reaches the detecting instrument. The filter must exclude unwanted wavelenths, and such a filter may be a quantity of the gas to be detected which is contained in a cell in the spectrometer. In one form radiation is chopped between an empty cell and the cell containing the gas to provide a modulated signal which gives information only on the radiation transmitted at frequencies near or at the centers of absorption lines of the gas. In another form, equivalent in performance to the first, the pressure of the gas in the cell may be altered at a regular frequency; this arrangement also gives a modulated signal, but requires a sophisticated and sensitive system of moving parts. In yet another form, the filter may comprise an optical interferometer with the cell of gas placed in one optical path, but this arrangement provides a fairly broad filter pass band compared with the other two forms, although it has the advantage of having no moving parts.

It is an object of the present invention to provide a filter having no mechanical moving parts and having a narrower band pass than has previously been possible.

According to the invention, a filter for a radiometer gas detector comprises an optical interferometer, having in each of first and second different optical paths therethrough a gas cell containing a quantity of the gas to be detected, there being a difference in pressure between the quantities of gas in the two gas cells, the gas cells being of substantially equal lengths in the direction of the optical paths therethrough, and the interferometer being arranged so that in the absence of the gas cells there is zero optical path difference between the said first and second optical paths through the interferometer.

The interferometer may be either a single pass or a double pass instrument, and will be either a Michelson interferometer or variations thereon.

Apparatus for detecting and/or measuring a gas in an atmosphere comprises a mechanical radiation-chopper, a wide band-pass filter of conventional type, a filter according to the present invention, a detector of radiation, and a phase sensitive detector connected to both the chopper unit and the detector of radiation and arranged to provide a d.c. output which varies in accordance with radiation from the gas in the atmosphere.

Normally the apparatus will operate at infra-red frequencies.

The mechanical chopper unit causes the radiation detector to produce an alternating current output which is easier to process than a d.c. output. The broad-band filter isolates a band of radiation in the area of interest. The apparatus will normally be calibrated before use.

The invention will now be described by way of example only with reference to the drawings filed with this specification in which:

FIG. 1 is a diagrammatic section of a prior art infrared filter;

FIGS. 1A and 1B illustrate output characteristics of the interferometer of FIG. 1 if one mirror is scanned away from zero optical path difference;

FIG. 2 is a diagrammatic section of a filter according to the present invention;

Figure 5:
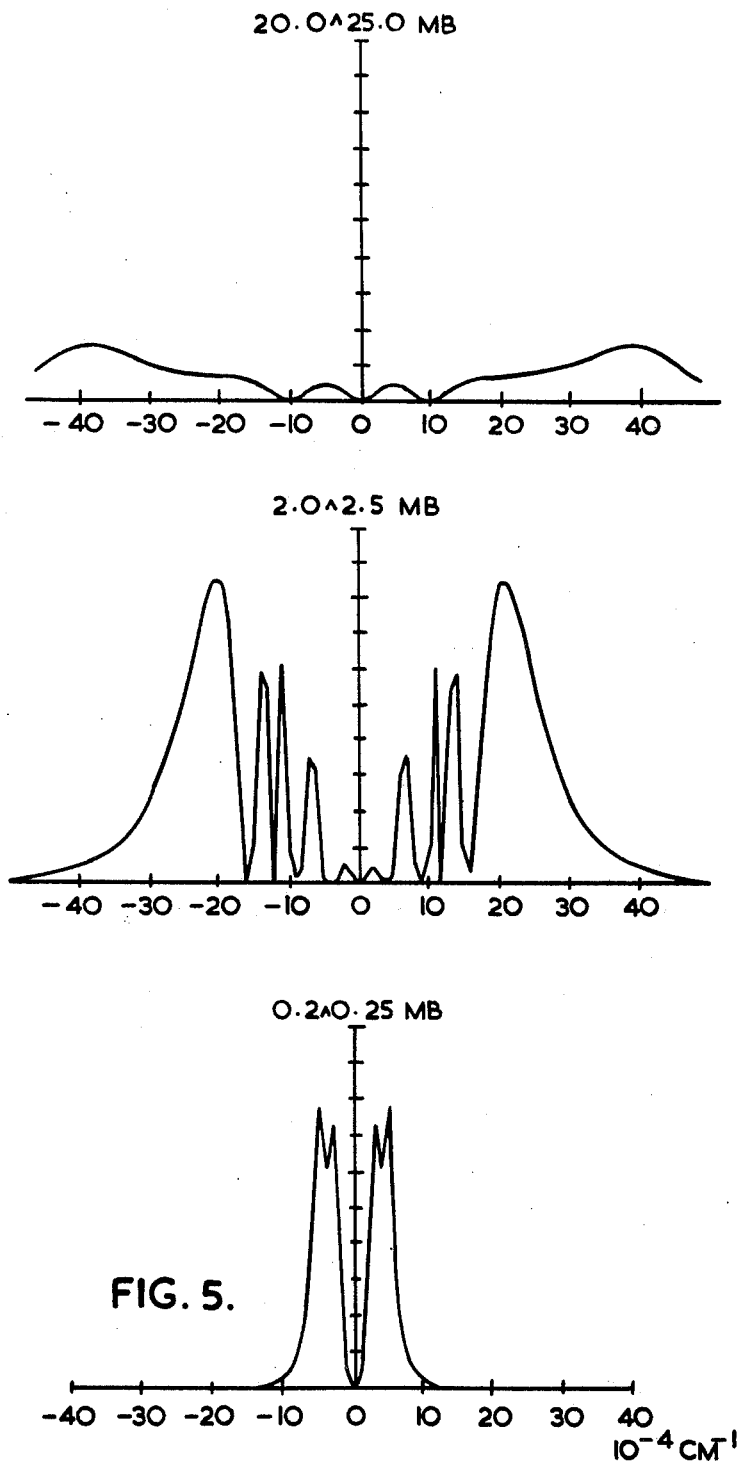

FIGS. 3(a), (b) and (c) illustrate the absorption coefficient and refractive index of a gas, and transmission at these wavelengths of the filter shown in FIG. 1;

FIGS. 4(a), (b) and (c) illustrate the absorption coefficient and refractive index of a gas, and transmission at these wavelengths of the filter according to the invention shown in FIG. 2;

FIG. 5 illustrates the effect on transmission of different pressures in the gas cells at a constant pressure ratio;

FIG. 6 illustrates the effect on transmission of different pressure ratios in the gas cells for constant pressure in one cell;

FIG. 7 illustrates the effect on transmission of gas cell length;

FIG. 8 illustrates a gas detection system;

FIG. 9 illustrates an arrangement for calibrating a gas detection system, and

FIG. 10 is a diagrammatic section of a double-pass filter according to the invention.

The optical characteristics shown in FIGS. 3 to 7 are based on calculations assuming the gas cells are 1cm long and contain $CO_2$ gas at about 0.2 millibars, that the 15 $\mu$m infra-red wavelength band is studied, and that the absorption line is Lorentzian in shape. However, it can be shown that very similar results are given for other line shapes such as those known as Van Vleck-Weisskopf and Zhevakin-Naumov. The wave number of the center of the line used in the calculations is 667.00cm$^{-1}$, and line half width is 0.2cm$^{-1}$atm$^{-1}$.

In FIG. 1, which shows a prior art filter, a Michelson interferometer consists of two roofed right angle mirrors 10, 12, and a beam splitter 14 having equal transmittance and reflectance, arranged as shown. A source of infra-red radiation is indicated by reference 16 and the paths taken by the radiation as it traverses the interferometer are shown by the arrowed lines. The mirrors 10, 12 are set to zero optical path difference. There are two outputs A and B, and FIGS. 1A and 1B show the respective outputs which would be obtained if one of the mirrors were scanned away from zero optical path difference; ie at zero optical path difference output B shows zero signal and output A shows a maximum signal, the two outputs being the complement of each other and alternate dark and light fringes occurring adjacent the central signal.

Consider now the insertion of a cell 18 containing a gas into one optical path of the interferometer. A gas absorbs infra-red radiation at characteristic absorption lines, see FIG. 3(a), and the refractive index of the gas changes at wavelengths near these lines as shown for one line in FIG. 3(b). The effect of the introduction of the gas cell 18 is to alter the optical path of radiation passing through it by different amounts depending on wavelength, so that near an absorption line dark and light fringes will be observed. At wavelengths away from an absorption line, no change in refractive index occurs, the optical path is not altered and a dark fringe only is observed at output B (FIG. 2). Thus, the combination of Michaelson interferometer and one gas cell acts as a selective filter, passing radiation only at wavelengths near the absorption lines of the gas in the cell. But the filter is broad in comparison with the line width as can be seen in FIG. 3(c), which shows the transmission curve of the filter, so that considerable amounts of "stray" radiation are allowed through.

A filter according to the invention is shown in FIG. 2, in which a Michelson interferometer 50, 52, 54 as before has arranged within it two gas cells, 58, 60, one in each radiation path, the cells being of identical size but containing quantities of the same gas at different pressures e.g. 0.20 and 0.25 millibars. The optical characteristics of the filter are shown in FIG. 4.

It can be seen that the transmission co-efficient is very markedly narrower in FIG. 4 than in FIG. 3 and is mainly in the form of two lobes on either side of the center of the absorption line. Consequently a very narrow band pass filter is produced.

It can be shown theoretically that the transmission of the interferometer at a particular wavelength depends on the difference between the refractive indices of the quantities of gas in the cells at their respective pressures. Near the center of an absorption line, refractive index is pressure dependent, so a difference exists between the quantities of gas in the respective cells and transmission occurs. Away from the center of an absorption line the refractive index of the gas is pressure independent; there is therefore no difference in refractive index of the gas as between the two cells, and hence no transmission. The wavelength range of pressure dependence is very narrow, so that a narrow bandwidth filter results.

In FIG. 2, the pressure in cells 58, 60 is 0.20 and 0.25 millibars and in FIGS. 4(a) and (b) the solid line corresponds to transmission through cell 58 and the crosses to transmission through cell 60. The refractive indices are very similar and differ by a small amount only near the line center; the difference is not visible in FIG. 4.

The length of each cell is conveniently 1cm, but a longer or shorter cell can be used; however, the cells should be equal in length to within a few microns. The pressure difference may be between 1 and 100% of the higher pressure, and the pressure may be between 0.2 and 25 millibars but higher or lower pressure and pressure differences may be used. Each cell is conveniently constructed with fused quartz spacers and windows made of germanium or zinc selenide or, provided a dry atmosphere is used, potassium bromide. The windows must be flat to within 1 micron. A window thickness from about 5 to 10 mm is generally suitable, but for each window material a compromise must be made between optical absorption — which increases with thickness — and the strength of the window, which must be able to withstand a pressure difference of up to about 1 atmosphere. The requirements of cell construction are well within the limits of standard optical techniques.

For quartz spacers, the temperatures of the two cells need to be kept equal to within about 10° C, which is easily achieved in the small volume occupied by the filter.

It is assumed that the beam splitter in the interferometer has transmittance = reflectance. In practice, if $r = Qt$, $Q$ may not always equal 1, but may vary from 0.8 to 1.0. It may therefore be necessary to provide a "grey" attenuator in the transmission arm as a compensator. Alternatively, a mechanical aperture could be used to provide attenuation.

A filter according to the invention is suitable for use in a filter radiometer for detecting any gas which can be contained in a gas cell for long periods, such as the gases $H_2O$, $O_2$, $CO_2$; $N_2O$, $NO$, $NO_2$, $SO_2$, $H_2S$, $CH_4$, $CO$, $CF_2CL_2$, $CF_3Cl$, $CFCl_3$. Possibly the following gases may be detected: $HNO_3$, $H_2O_2$, $NH_3$, $H_2SO_4$, $HCl$ and organic gases such as aldehydes.

It is a particular advantage of the present invention that by alteration of the variables, eg pressure and pressure difference, the shape and position of the side lobes can be altered so that the part of an absorption line to be studied can be selected.

FIG. 5 illustrates the effect of varying the pressure in cells 58, 60 but keeping the pressure ratio constant. Increasing pressure moves the side lobes progressively away from the center of the absorption line as shown by the middle and upper curves of FIG. 5. In FIG. 6 the pressure in one cell is kept at 0.2 millibars and the effect of altering the pressure ratio from 1:1.02 to 1:2 is shown—a greater difference in pressure moving the side lobes away from the center of the absorption line. FIG. 7 shows that increasing the cell length has a similar effect to increase in pressure or pressure ratio; L being length of cell in centimeters.

FIG. 8 shows a detector system employing a filter according to the invention. Radiation from an infra-red source 22 passes through a mechanical chopper unit 24 e.g. of the kind provided with rotatable blades or a rotatable apertured disc (to provide an a.c. signal in a detector, a.c. being easier to process than a d.c. signal), through a conventional wide band-pass filter 26 (to limit radiation passed to a selected infra-red band) to a filter according to the invention, indicated by reference 28. The wide band-pass filter 26 is conveniently of the multilayer interference kind, and for a detector for carbon dioxide in the atmosphere has a pass band from about 13 to about 17 $\mu$m centered on 15 $\mu$m. The filter 28 allows narrow bands of wavelengths near the centers of the absorption lines of the gas contained in its gas cells to pass through to a conventional infra-red detector 30, such as a pyroelectric detector operated at room temperature. The radiation path is indicated throughout by the broken line.

The radiation detector 30 is connected to a phase sensitive detector 32 which is also connected to the chopper unit; the electrical connections are shown by the full lines.

In operation, the pyroelectric detector produces an a.c. signal as the chopped radiation causes the crystal lattice to expand and contract. This a.c. signal is compared in phase with the phase of the chopper unit by the phase sensitive detector 32, which produces a d.c. output signal proportional to the strength of the signal falling on the detector 30.

Because the gas in the cells normally has several absorption lines in the band passed by filter 26, and radiation from all of these lines is transmitted simultaneously, an integration effect occurs and a considerable signal can be received.

A suitable frequency of operation of the chopper is between 10 and 1000Hz, for example 180Hz.

It is emphasized that although the chopper has moving parts, these can be robust and simple. The filter 28 does not itself have moving parts.

Before being used to measure the concentration of a gas, the apparatus shown in FIG. 8 must be calibrated. Referring to FIG. 9, for calibration the parts of the apparatus indicated by reference 21 in FIG. 8 are placed in an evacuated chamber 34 which also contains a substantially black source 36 cooled by liquid helium or liquid nitrogen cooling means 38. The source 36 simulates the cold background of space, and known pressures of the gas to be detected are introduced into the chamber, and thermally emit infra-red radiation. The corresponding readings are taken on the detector 30 in order to calibrate the instrument.

It may be that an error occurs in the system due to "leakage" transmission of radiation at wavelengths other than near the line centers. This may give rise to asymmetric transmission profiles.

A technique for reducing the effect of leakage transmission is to use a double pass Michelson interferometer such as that shown in FIG. 10 in which two roofed right-angle mirrors 60, 62 and a beam splitter 64 are arranged as before, but the parallel arms of the mirrors, 60(a), 62(a) are considerably extended. A plane mirror 66 is arranged to form the fourth side of a square. Two cells 70, 72 of gas at different pressures are included in the interferometer; the cells have larger apertures than the cells in FIG. 2 so that the "first pass" beams indicated by the arrowed full lines and the "second pass" beams indicated by the arrowed broken lines both pass through the gas cells.

The leakage radiation transmitted is a small fraction of the total in the arrangement of FIG. 2, and passing the radiation through the gas cells twice has a squaring effect, so that the effect of leakage transmission in a double-pass interferometer is very small indeed.

After calibration, a detecting system having a filter according to the invention may be used to measure the concentration of any gas which can be contained within its cells. The concentration to be measured may be that of a gas in the earth's atmosphere, and different layers of the atmosphere may be remotely studied by selected instruments. For example, stratospheric layers may be observed from a satellite or spacecraft, when the fact that the filter has no moving parts is advantageous. At these altitudes gaseous concentrations as low as $10^{-9}$ or even $10^{-11}$ may be detected. The system may also be used to provide maps of stratospheric water vapour or, using emissions from $CO_2$ or $O_2$ gases, of stratospheric temperatures.

The system may also be used at lower altitudes, e.g. in aircraft, or at ground level. For high gas concentrations, less accurately engineered instruments may be used. The system may be used as a continuous monitor for long periods without attention in contrast to the "wet chemistry" gas detectors, used at present, which need frequent skilled attention.

It has been stated that the distance, from an absorption line center, of the side lobes corresponding to transmitted wavelengths can be chosen by altering gas pressure or pressure ratio. It is known that the further from the line center the emitted wavelength, the further from the detector is the source of radiation. This is due to the fact that atmospheric absorption is strongest for wavelengths near the absorption line center, so that any received radiation must originate predominantly from a part of the atmosphere close to the detector. But for wavelengths corresponding to the side lobes of the absorption line, atmospheric absorption is much reduced, and radiation therefore can be received by the detector from more distant parts of the atmosphere. Hence the effect can be used to select the distance from the detecting system of the layer of the atmosphere observed by the system. Thus emissions from different levels of the stratosphere can be observed, or low level gases at high concentrations can be measured from the earth's surface. Depending on gas concentration and pressure, absorption line widths of between $10^{-4}$ and $10^{-1} cm^{-1}$ may be studied.

In a detecting system in e.g. a satellite, it may be advantageous to replace the mechanical chopper unit by a "Doppler chopping" system. The direction of viewing is arranged to be perpendicular to the direction of motion, and the field of view is oscillated about its mean direction, e.g. by $\pm 5°$. The incoming radiation is then seen with a varying Doppler-shifted frequency, and atmospheric emission lines are scanned across the filter transmission profile.

I claim:

1. A radiation filter, for a gas detector, comprising an optical interferometer having in each of first and second different optical paths therethrough a gas cell containing a quantity of the gas to be detected; there being a difference in pressure between the quantities of gas in the two gas cells; the gas cells being of substantially equal lengths in the direction of the optical paths therethrough; and the interferometer being arranged so that in the absence of the gas cells there is zero optical path difference between the said first and second optical paths through the interferometer.

2. A radiation filter according to claim 1 in which the interferomter is a Michelson interferometer.

3. A radiation filter according to claim 1 arranged as a double-pass instrument in which at least some of any radiation passing through the filter passes twice through each of the gas cells.

4. A radiation filter according to claim 1 arranged so as to be operative in the infra red part of the radiation spectrum.

5. A radiation filter according to claim 4 in which each gas cell has a spacer of fused quartz.

6. A radiation filter according to claim 4 in which each gas cell has windows of germanium.

7. A radiation filter according to claim 4 in which each gas cell has windows of zinc selenide.

8. A radiation filter according to claim 4 in which each gas cell has windows of potassium bromide.

9. A radiation filter according to claim 1 in which the pressure difference between the quantities of gas in the two gas cells is between 1 and 100% of the higher gas pressure.

10. A gas detector, for detecting a gas in an atmosphere by radiation from said gas, having arranged successively along an optical path for said radiation a radiation-chopper; a wide band-pass filter; a radiation filter comprising an optical interferometer having in each of first and second different optical paths therethrough a gas cell containing a quantity of the gas to be detected, there being a difference in pressure between the quantities of gas in the two gas cells, the gas cells being of substantially equal lengths in the direction of the optical paths therethrough, and the interferometer being arranged so that in the absence of the gas cells there is zero optical path difference between the said first and second optical paths through the interferometer; a radiation detector; and electrically connected both to the radiation detector and the radiation-chopper a phase-sensitive detector arranged to provide an electrical output which varies in accordance with radiation received by the gas detector from said gas.

11. A gas detector according to claim 10 in which the radiation-chopper is a mechanical chopper.

12. A gas detector according to claim 10 in which the radiation-chopper imposes on the received radiation an oscillating Doppler frequency shift.

* * * * *